United States Patent
Baer

(10) Patent No.: US 10,828,392 B2
(45) Date of Patent: Nov. 10, 2020

(54) METHOD FOR PREPARING A THREE-DIMENSIONAL POLYMER SCAFFOLD FOR TISSUE ENGINEERING

(71) Applicant: Hans U. Baer, Freienbach (CH)

(72) Inventor: Hans U. Baer, Freienbach (CH)

( * ) Notice: Subject to any disclaimer, the term of this patent is extended or adjusted under 35 U.S.C. 154(b) by 0 days.

(21) Appl. No.: 15/755,128

(22) PCT Filed: Aug. 25, 2016

(86) PCT No.: PCT/EP2016/070086
§ 371 (c)(1),
(2) Date: Feb. 26, 2018

(87) PCT Pub. No.: WO2017/032837
PCT Pub. Date: Mar. 2, 2017

(65) Prior Publication Data
US 2018/0250437 A1  Sep. 6, 2018

(30) Foreign Application Priority Data
Aug. 27, 2015  (EP) .................................... 15182725

(51) Int. Cl.
A61L 27/24  (2006.01)
A61L 27/34  (2006.01)
A61L 27/56  (2006.01)

(52) U.S. Cl.
CPC .............. *A61L 27/24* (2013.01); *A61L 27/34* (2013.01); *A61L 27/56* (2013.01); *A61L 2400/18* (2013.01)

(58) Field of Classification Search
CPC .......... A61L 27/24; A61L 27/34; A61L 27/56; A61L 2400/18
USPC ........................................................ 424/93.1
See application file for complete search history.

(56) References Cited

U.S. PATENT DOCUMENTS

| 2001/0054374 A1* | 12/2001 | Omatsu ..................... A61L 2/28 116/206 |
| 2007/0166343 A1 | 7/2007 | Goerne et al. |
| 2010/0317080 A1 | 12/2010 | Zimmermann et al. |
| 2011/0071227 A1 | 3/2011 | Ahlers et al. |

FOREIGN PATENT DOCUMENTS

| EP | 1 787 664 A1 | 5/2007 |
| EP | 2256155 A1 | 12/2010 |
| EP | 2 716 305 A1 | 4/2014 |
| EP | 2815773 A1 | 12/2014 |
| JP | 2007-282514 A | 11/2007 |
| JP | 2010-518925 A | 6/2010 |
| JP | 2011-523425 A | 8/2011 |
| JP | 2014-522277 A | 9/2014 |
| WO | 2006/021992 A1 | 3/2006 |
| WO | 2014/103688 A1 | 7/2014 |

OTHER PUBLICATIONS

Pignata et al., Low-temperature, low-pressure gas plasma application on *Aspergillus brasiliensis, Escherichia coli* and pistachios, Journal of Applied Microbiology, 116, (2014), p. 1137-1148.*
Baldino, Lucia et al., "Complete glutaraldehyde elimination during chitosan hydrogel drying by SC-CO2 processing.", The Journal of Supercritical Fluids, vol. 103, pp. 70-76, (2015).
Mooney, David J. et al., "Novel approach to fabricate porous sponges of poly(D, L-lactic-co-glycolic acid) without the use of organic solvents.", Biomaterials, vol. 17, No. 14, pp. 1417-1422, (1996).
Oct. 24, 2016 International Search Report issued in Patent Application No. PCT/EP2016/070086.
Feb. 27, 2018 International Preliminary Report on Patentability issued in Patent Application No. PCT/EP2016/070086.
May 8, 2020 Office Action issued in Chinese Patent Application No. 201680049573.0.
Apr. 7, 2020 Office Action issued in Japanese Patent Application No. 2018-510458.
Zhu T. et al., "Decomposition of Formaldehyde With Non-Thermal Plasma", Journal of Beijing University of Technology, vol. 34, No. 9, pp. 971-975 (Sep. 2008).

* cited by examiner

Primary Examiner — Jennifer M. H. Tichy
(74) Attorney, Agent, or Firm — Oliff PLC

(57) ABSTRACT

A method for preparing a three-dimensional polymer scaffold (3D-PS) for use in tissue-engineering, the method including the subsequent steps of: providing a polymeric precursor scaffold (p-PS) having at least one biodegradable natural polymer ($P_A$); treating the polymeric precursor scaffold (p-PS) with a cross-linking agent having glutaraldehyde to induce cross-linking of the natural polymer ($P_A$), thereby forming a cross-linked polymer scaffold (x-PS) and subjecting the cross-linked polymer scaffold (x-PS) of step b) to low-pressure plasma treatment involving exposure of the polymer scaffold to an ionized oxygen-containing gas plasma at a pressure in the range of $10^{-3}$ to $10^{-6}$ bar and a temperature below 40° C.

8 Claims, 1 Drawing Sheet

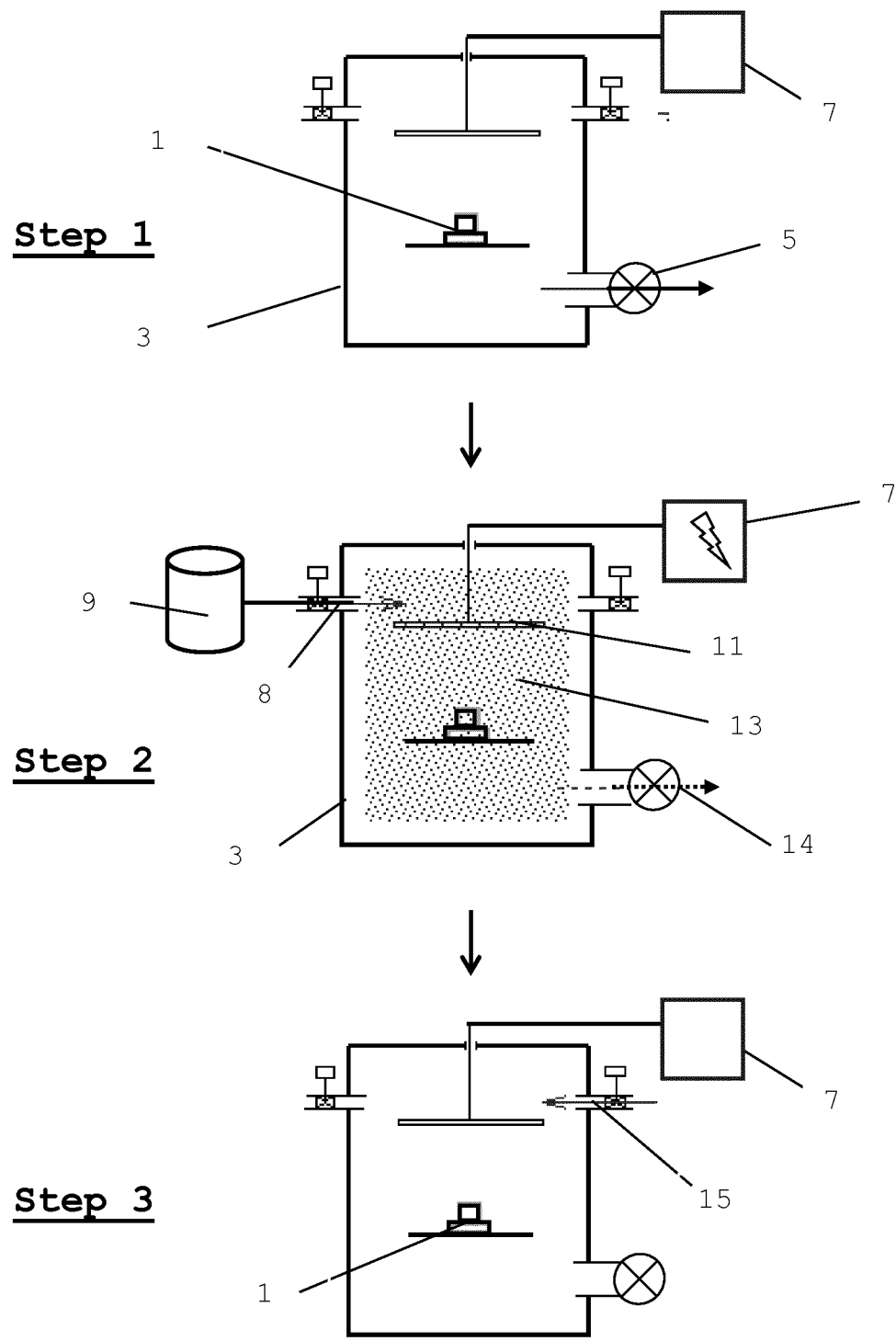

METHOD FOR PREPARING A THREE-DIMENSIONAL POLYMER SCAFFOLD FOR TISSUE ENGINEERING

The present invention relates to a method for preparing a three-dimensional polymer scaffold for tissue engineering according to claim 1.

Tissue engineering is an interdisciplinary field which combines engineering and material sciences with medicine and provides an alternative approach in the treatment of malfunctioning or lost organs. In this approach, temporary three-dimensional scaffolds (also called matrices) serve as an adhesive substrate for the implanted cells and a physical support to guide the formation of the new organs. Such three-dimensional scaffolds are therefore utilized to guide the process of tissue development by delivering cells to desired sites in the body, defining a potential space for engineered tissue, and promoting cell growth. In order to enable these processes, scaffolds for tissue engineering should meet the following criteria:

The surface should permit cell adhesion, promote cell growth, and allow the retention of differentiated cell functions. Further, the three-dimensional scaffolds should be biocompatible and biodegradable such that the scaffold structures can eventually be eliminated in vivo without causing inflammation or toxic degradation by-products. With regard to their structure, the porosity of the scaffolds should be high enough to provide sufficient space for cell adhesion, extracellular matrix regeneration, and minimal diffusional constraints during culture. Their pore structure should allow even spatial cell distribution throughout the scaffold to facilitate homogeneous tissue formation and the material should be reproducibly processable into three-dimensional structure, as well as mechanically strong.

A number of three-dimensional porous scaffolds or "matrices" fabricated from various kinds of biodegradable materials have been developed. EP-A-2256155, for instance, discloses porous matrices based on a biologically compatible polymer or polymer mixture. According to this document, the porous matrices are prepared by a so-called particulate leaching procedure in which a mixture composed of at least partly dissolved polymer particulates and solid salt particulates having a defined grain size is compacted and the salt particles are subsequently leached out. Alternatively, a so-called "gas foaming" method may be used, as described for instance by D. J. Mooney et al "Novel approach to fabricate porous sponges of poly(D,L-lactic-co-glycolic acid) without the use of organic solvents" in Biomaterials, 17, 1417-1422, 1996.

Nowadays, porous scaffolds for tissue-engineering often comprise synthetic biodegradable polymers since they are easily formable into desired shapes and have better mechanical strengths than naturally derived polymers. Synthetic biodegradable polymers have the additional advantage that their periods of degradation can also be manipulated by controlling the crystallinity, molecular weight, and copolymer ratio.

However, despite their advantages, three-dimensional scaffolds comprising synthetic polymers also suffer from several limitations such as the lack of cell-recognition signals, toxicity, limited biological acceptance and functional capacity. A further limitation is that synthetic polymers are generally hydrophobic, as indicated by high contact angles with water, which has been found to have a strongly negative impact on cell attachment and cell seeding activities on the scaffolds. In particular, if hydrophobic implants are implanted into the human body, they can cause tissue irritation, edema and scarring.

Looking for ways to improve the hydrophilic properties of the scaffolds, the use of collagen-based biomaterials in the field of tissue engineering has been intensively growing over the past decades. Apart from its hydrophilic properties, collagen possesses a major advantage in being biodegradable, biocompatible, easily available and highly versatile. In addition, the ability of collagen to polymerize into a three-dimensional fibrous scaffold makes it an appealing material for extensive therapeutic applications. However, since collagen is a natural protein, it remains difficult to sterilize it without alterations to its structure. As a further downside, collagen scaffold constructs lack desired mechanical properties for the preparation of medical implants for use in tissue engineering. In particular, hydrated reconstituted collagenous scaffolds are mechanically weak and stiff. Therefore, multiple cross-linking methods were investigated and different combinations with other (bio)polymers were explored in order to improve tissue function and mechanical stability of the resulting scaffold.

Cross-linking involves the use of physical or chemical cross-linkers, which form covalent bonds between characteristic chemical groups on natural polymers. Cross-linking techniques are especially important for the preparation of natural polymer scaffolds, e.g. scaffolds from collagen-based biomaterials, to enhance their mechanical and enzymatic resistance properties for implantation purposes.

One of the most prominent protein cross-linking agents in protein chemistry is glutaraldehyde—owing to its low cost, high reactivity and high solubility in aqueous solution. Apart from these benefits, glutaraldehyde has proven to be highly valuable in the preparation of three-dimensional scaffolds from natural polymers, in particular collagen, for tissue engineering purposes, since it greatly enhances the stability of the cross-linked tissue while significantly reducing antigenicity and biodegradation. Specifically, natural polymer scaffolds comprising collagen that have been cross-linked with glutaraldehyde have enhanced mechanical and enzymatic resistance properties but retain many of the viscoelastic properties of the native collagen fibrillar network, which render them suitable for bioprostheses.

On the downside, glutaraldehyde is rather toxic even in relatively low concentration and it was found that bioprostheses or implants processed with glutaraldehyde give rise to inflammatory reactions and are the subject of calcification in the long term. Furthermore, an additional detrimental side effect of glutaraldehyde treatment is the tendency of such treated tissues to release cytotoxic by-products, such as monomeric glutaraldehyde, hemiacetals and alcohol condensation products, into the surrounding environment. Persistent, low-grade local tissue inflammation is common as a result of these by-products and cell growth on these treated biomaterials is markedly diminished.

The summated result is, thus, that the use of glutaraldehyde-treated scaffolds in tissue engineering is very limited. Therefore, intensive research is currently done with the goal to develop less toxic chemical cross-linkers to replace glutaraldehyde. Potential candidates have been found in the carbodiimide family (Everaerts, F. et al, *J. Biomed. Mater. Res. A* 2008, 85, 547-555), and also the isocyanate chemical family, especially hexamethylene diisocyanate, is used to crosslink natural polymers, in particular collagen, scaffolds (Zeugolis, D. I. et al, *J. Biomed. Mater. Res. A* 2009, 89, 895-908). A further interesting alternative is Genipin, a chemical cross-linker derived from a vegetal source, which shows a high potential to replace glutaraldehyde because of its low toxicity (Sundararaghavan, H. G. et al, *J. Biomed. Mater. Res. A* 2008, 87, 308-320). Nonetheless, all these chemical stabilisation techniques leave potentially toxic residues in the cross-linked biomaterial and there is still a great need for alternative ways to produce stable three-dimensional cross-linked polymer networks.

It is therefore an object of the present invention to provide a method for preparing a biocompatible and biodegradable three-dimensional polymer scaffold for use in tissue engineering, which is essentially free from toxic residues and allows for efficient cell retention and proliferation.

This object is achieved by the method for preparing a three-dimensional polymer scaffold comprising at least one natural polymer, i.e. a naturally derived polymer, according to claim 1. Preferred embodiments are subject of the dependent claims.

According to one aspect, the present invention provides a method for preparing a three-dimensional polymer scaffold for use in tissue-engineering, said method comprising the subsequent steps of
a) providing a polymeric precursor scaffold (p-PS) comprising at least one biodegradable natural polymer ($P_A$), preferably selected from the group consisting of collagen, gelatin, laminin, fibrinogen, albumin, chitin, chitosan, agarose, hyaluronic acid alginate and mixtures thereof;
b) treating the polymeric precursor scaffold (p-PS) with a cross-linking agent comprising glutaraldehyde to induce cross-linking of the natural polymer ($P_A$), thereby forming a cross-linked polymer scaffold (x-PS);
c) subjecting the cross-linked polymer scaffold (x-PS) of step b) to low-pressure plasma treatment involving exposure of the polymer scaffold to an ionized oxygen-containing gas plasma at a pressure in the range of $10^{-3}$ to $10^{-6}$ bar and a temperature below 40° C., thereby affording a three-dimensional polymer scaffold (3D-PS).

The present invention therefore provides a method that allows for preparing a cross-linked scaffold (x-PS) from at least one natural polymer ($P_A$), whereby the cross-linked polymer scaffold (x-PS) is subsequently subjected to plasma treatment in order to provide a biocompatible three-dimensional polymer scaffold (3D-PS) that is highly hydrophilic and free from toxic substances, which makes it particularly well suited for use in medical applications, in particular for tissue engineering.

The term "Plasma treatment" is a common name for a variety of industrial applications of plasma, such as cleaning, coating and/or altering the surface of various organic and synthetic substrates. For instance, various types of coatings may be applied, depending on the plasma material. More specific examples of plasma treatments include etching of semiconductor chips, deposition of silicon for solar cell production, deposition of silicon dioxide for passivation of surfaces, as well as melting and welding with plasma arcs.

The term "plasma" thereby generally refers to an excited and radicalized gas, i.e. an electrical conducting process gas involving electrons and ions. Plasma is commonly generated by means of electrodes in a vacuum chamber (so-called "RF plasma approach"), but it can also be generated using capacitive or inductive methods, or microwave radiation. The most important process gases are oxygen, hydrogen, nitrogen, tetrafluoromethane, argon, helium, sulfur hexafluoride, air, water and mixtures of these gases.

Even though basically every material surface can be plasma treated, it has proven difficult to treat heat-sensitive materials, since energy conversion efficiency of plasma treatment generally increases with temperature. Therefore, plasma treatment at lower temperature requires much longer process times, which increases the risk that the structure of the treated material suffers under the treatment.

In spite of these facts, it was surprisingly found that plasma treatment under the conditions defined in step c) of the method of the present invention does not negatively affect biocompatibility or stability of the polymer scaffold, but even provides it with especially favourable properties for the adhesion and growth of cells.

In particular, it has been found that plasma treatment of the cross-linked polymer scaffold (x-PS) obtained in step b) of the inventive method not only activates the surface and enhances the scaffolds' hydrophilicity but also allows for essentially complete removal of any glutaraldehyde residue of the cross-linking agent from the cross-linked polymer scaffold, without alteration of the structure of natural polymer ($P_A$). Since the three-dimensional polymer scaffold obtainable by the method of the present invention is for use in the field of tissue engineering, these findings are of major importance:

On the one hand, the activation of the scaffold's surface and the increased hydrophilicity of the polymer scaffold is particularly important for materials that are intended for use as a substrate for cell cultures, as hydrophilic surfaces facilitate the adhesion of cells thereto.

On the other hand, since any glutaraldehyde residue that is present on the prepared three-dimensional polymer scaffold will limit the intended use thereof as an implant substrate in medical applications due to the above-described release of cytotoxic by-products and occurrence of calcification of glutaraldehyde-treated materials, an essentially complete removal of glutaraldehyde from the cross-linked polymer scaffold, i.e. an essentially complete detoxification, is a huge asset as it allows for using the glutaraldehyde-treated polymer scaffold in a therapeutic treatment.

As such, by the plasma-treatment step c) as defined in claim 1 of the present application the present invention provides the key that allows for using natural polymers with their favourable biocompatible properties and the excellent cross-linking capacity of glutaraldehyde to prepare a stable, biodegradable and biocompatible porous scaffold that can readily be used in medical applications, and in particular as cell seeding substrate for tissue engineering.

For the plasma treatment in step c) of the method of the present invention it is preferred that the cross-linked polymer scaffold (x-PS) is subjected to plasma treatment for a period of 0.5 to 60 minutes, preferably 2 to 30 minutes, most preferably about 10 minutes. If the plasma treatment is less than 30 seconds, the described effects, i.e. removal of glutaraldehyde, activation of the surface and cleaning of the polymer scaffold, are not achieved. If the treatment is longer than one hour, it is likely that the three-dimensional polymer scaffold will be damaged.

For further promoting detoxification of the cross-linked polymer scaffold (x-PS), i.e. for promoting essentially complete removal of glutaraldehyde residues, it is preferred that step b) involves at least one of the following steps b') to b''''):
step b') involving a treatment of the cross-linked polymer scaffold (x-PS) with an aqueous blocking agent, preferably glycine and/or glutamic acid aqueous solution;
step b'') involving the suction of a gas (or gas mixture), preferably selected from the group consisting of gaseous glycine, gaseous glutamic acid, oxygen and/or an inert gas, through the cross-linked polymer scaffold (x-PS);
step b''') involving a treatment of the cross-linked polymer scaffold (x-PS) under reduced pressure by multiple application of vacuum for less than 1 s, preferably for less than 1 ms, most preferably for about 0.1 ms; and step b"") involving freeze-drying of the cross-linked polymer scaffold (x-PS) to remove excess glutaraldehyde.

Step b) of the inventive method may, thus, encompass one or all of preferred steps b'), b") and b'").

Step b') involves a treatment of the cross-linked polymer scaffold (x-PS) with an aqueous blocking agent to block non-reacted glutaraldehyde groups. Preferred blocking agents include glycine and glutamic acid. Most preferably, the scaffold is first treated with glycine aqueous solution and subsequently with glutamic acid aqueous solution. However, other blocking agents, e.g. casein, albumin, gelatin or methanol-acetic anhydride, may also be used.

Step b") involves suction of a gas through the cross-linked polymer scaffold (x-PS). Preferred gases include gaseous blocking agents, in particular gaseous glycine or glutamic acid, oxygen, and/or inert gases, such as nitrogen, helium, neon, argon, xenon etc. Thus, instead of using an aqueous blocking agent as described above for step b') a gaseous blocking agent can be used that is then sucked through the cross-linked polymer scaffold. Suction of the gas through the scaffold can be performed, for instance, by placing the scaffold inside a tube, into which the gas is fed at one end and sucked out at the other end. The use of gaseous blocking agents instead of aqueous solutions has the advantage that additional drying procedures, such as freeze-drying, can be facilitated or even omitted.

Step b'") involves a treatment of the of the cross-linked polymer scaffold (x-PS) under reduced pressure by multiple application of vacuum for a very short time. The short treatment time is crucial because, if vacuum is applied for several seconds or longer, the temperature at the surface of the polymer scaffold will rise above 40° C., which will damage the structure of the natural polymer ($P_A$). For that reason, it is preferred that the scaffold is set under vacuum for less than 1 s, preferably less than 0.5 s, more preferably for about 1 ms, most preferably for about 0.1 ms. This procedure is repeated multiple times, preferably over 50 times. This allows for drying the cross-linked polymer scaffold (x-PS) and removing excess natural polymer and glutaraldehyde without damaging the cross-linked structure of the polymer scaffold.

Step b"") involves freeze-drying, also known as lyophilization, which is a dehydration process typically used to preserve a perishable material or make the material more convenient for transport. Freeze-drying works by freezing the material and then reducing the surrounding pressure to allow the frozen water in the material to sublimate directly from the solid phase to the gas phase.

In a preferred embodiment, the method further comprises a step d), in which the plasma-treated three-dimensional polymer scaffold (3D-PS) of step c) is exposed to a second ionized gas plasma that is different from the first gas plasma and is selected from the group consisting of helium, argon, nitrogen, neon, silane, hydrogen, oxygen and mixtures thereof. Most preferably, the second ionized gas plasma is hydrogen or nitrogen. The treatment of the three-dimensional polymer scaffold (3D-PS) with a second gas plasma further promotes activation of the scaffold's surface, which facilitates adhesion and growth of cells on the polymer scaffold.

In a particularly preferred embodiment, the three-dimensional polymer scaffold (3D-PS) obtained after step c) or d) is subsequently sterilized by treating the polymer scaffold with hydrogen peroxide, preferably in form of an ionized hydrogen peroxide gas plasma, at a temperature below 40°, preferably below 35°. The hydrogen peroxide gas plasma is preferably generated by the same device that is used for generating the ionized oxygen-containing gas plasma in step c) of the method according to the present invention. For sterilization purposes, the hydrogen peroxide treatment of the three-dimensional polymer scaffold is preferably conducted for a time period of at least 1 hour, preferably of about 10 hours, most preferably of about 16 hours.

It has been surprisingly found that the above-described sterilization conditions allow for perfect sterilization of the scaffold, without using any of the conventional sterilization techniques involving hot steam, gamma rays, electron beam irradiation or harsh chemical treatments. Avoiding the aforementioned conventional sterilization means is of particular importance for natural polymer scaffolds, e.g. collagenous scaffolds, since natural polymer scaffold structures—either cross-linked or decellularized—are relatively fragile and temperature sensitive. Due to this sensitivity, conventional sterilization methods were shown to cause alteration or even degradation of the molecular structure of the natural polymer scaffold, which not only decreases its mechanical and enzymatic resistance but also reduces its hydrophilic properties.

Thus, in contrast to conventional techniques, sterilization of the three-dimensional polymer scaffold according to the present invention can be achieved by the direct effect of reactive gases, specifically hydrogen peroxide gas plasma. If desired, plasma-generated UV light can additionally or alternatively be applied to kill bacteria. As such, the method of the present invention allows for cleaning and sterilizing heat-sensitive biomaterials, such as scaffolds comprising a natural polymer, without damaging the 3D-structure of the biomaterial.

As regards the natural polymer ($P_A$), said polymer is preferably selected from the group consisting of collagen, gelatin, laminin, fibrinogen, albumin, chitin, chitosan, agarose, hyaluronic acidlalginate and mixtures thereof, whereby collagen and laminin are preferred.

From the above-mentioned natural polymers ($P_A$), collagen is most preferred. Thanks to its nano-fibrous architecture collagen is particularly effective in promoting cell adhesion, growth and differentiated function in tissue cultures. However, it has also been found that if the natural polymer ($P_A$) comprises collagen, the hydrophilic properties of the three-dimensional polymer scaffold according to the present invention are particularly enhanced. In this regard, the term "collagen" as used in the context of the present invention encompasses naturally derived collagens and synthetically produced collagens and also collagen derived substances, such as gelatine, which is a hydrolysed form of collagen.

In a preferred embodiment, the natural polymer ($P_A$) essentially consists of collagen. In this regard, the natural polymer ($P_A$) may consist of only one type of collagen, i.e. type I, or may consist of a mixture of collagen types, e.g. a mixture of type I collagen and type IV collagen. In the latter case, preference is given to the mixture containing the proteins in approximately equal percentages by weight. Collagen type I is most preferred, since it is one of the main components of natural blood vessels and provides the secondary structure with cellular attachment sites as well as tensile strength.

According to a particularly preferred embodiment, the polymeric precursor scaffold (p-PS) provided in step a) of the inventive method further comprises a second biodegradable polymer ($P_B$) different from natural polymer ($P_A$), whereby the polymeric precursor scaffold (p-PS) is prepared by a process comprising the steps of i) providing a basic porous scaffold (bPS) made from at least the second biodegradable polymer ($P_B$);

ii) introducing a polymer solution comprising the biodegradable natural polymer ($P_A$) dissolved in a polymer solvent ($S_A$) into pores of the basic porous scaffold (bPS), whereby the concentration of the natural polymer ($P_A$) in the polymer solvent ($S_A$) is preferably in the range from 0.1 to 5.0 (w/v) %, more preferably from 0.1 to 1.5 (w/v) %; and iii) removing the polymer solvent ($S_A$) under reduced pressure, preferably by freeze-drying.

The use a polymeric precursor scaffold (p-PS) prepared in accordance with the process described above in the method of the present invention will lead to a three-dimensional polymer scaffold that preferably comprises a porous structure formed by the second polymer (Pb) that comprises pores in which the natural polymer ($P_A$) is contained. Preferably, the natural polymer ($P_A$) also forms a porous structure, e.g. in the form of fibrils, fibers or foams, within the pores of the second polymer ($P_B$). In this special type of "scaffold in scaffold" matrix, the polymeric structure of the second polymer ($P_B$) will generally provide physical stability to the matrix, whereas the natural polymer ($P_A$) provides a cell-friendly environment, which increases the survival and proliferation rate of cells within the three-dimensional polymer scaffold (3D-PS).

The word "pores" is hereby used to designate the cavities or void regions which are present in the three-dimensional polymer scaffold according to the invention. They may have a round shape and/or an angular, in particular octagonal, shape in a 2-dimensional section and/or a canted shape when seen 3-dimensionally. The shape is furthermore preferably characterized by extensions such that the shape of the cavities can be compared with the shape of nerve cells. As such, the term "pores" also refers to cavities formed by filaments enclosing a void region. These pores or cavities may also be interconnected, meaning that the pore walls between two adjacent pores can comprise holes, forming a connection between said adjacent pores. In this regard, it is to be noted that the pores formed by the natural polymer ($P_A$) and those of the second polymer ($P_B$) may be structurally distinct from one another, e.g. with regard to their shape, size and/or interconnectivity. As such, the cavities formed by single and/or interconnected pores can accommodate one or multiple different types of cells. For example, in one embodiment the pores formed of the second polymer ($P_B$) may provide sufficient void space for accommodating cells of larger cell size, whereas the porous structure formed of the natural polymer ($P_A$) within the pores formed by the second polymer ($P_B$) may provide smaller pores for retaining cells of smaller cell size. The three-dimensional polymer scaffold (3D-PS) according to the present invention is therefore also particularly well suited for embedding and seeding cells of more than one cell type.

It was further found that the shape and dimensions of the cavities can influence the growth behaviour and biological interactions of cells cultivated on the three-dimensional polymer scaffold (3D-PS). Specifically, an interconnected porous structure formed by pores of the second polymer ($P_B$) and the natural polymer ($P_A$) enables a cell-to-cell-interaction within the three-dimensional polymer scaffold. This not only increases the survival rate of cells cultivated on the polymer scaffold but the cells were even found to spontaneously form functional micro tissues mimicking various body tissues. For instance, hepatocytes were found to form strings of self-organized interacting cells mimicking liver tissue. On the other hand, if cells of endothelial origin were cultivated on the three-dimensional polymer scaffold, they were found to spontaneously form micro capillaries within the polymer scaffold. If the polymer scaffold is then implanted into living tissue, the newly-formed micro capillaries can connect to existing capillaries in the implantation site, which enables circulation between the living tissue and the three-dimensional polymer scaffold.

The polymer solvent ($S_A$) used in step ii) of the process described above is preferably an aqueous solvent, more preferably an acidic aqueous solvent. The use of an aqueous solvent allows for removing it by freezing at −80° C. and/or lyophilisation under vacuum. Times of about 3 h to 60 h, and, in particular, in the range of from about 12 h to 36 h, under vacuum have proved to be expedient for removal of the polymer solvent ($S_A$).

A centrifugation step is preferably performed before removing the polymer solvent ($S_A$) under reduced pressure. The centrifugation step serves to remove any excess of the dissolved natural polymer ($P_A$) that is not adhering to the basic porous scaffold (bPS) of the second polymer ($P_B$).

In a particularly preferred embodiment, the natural polymer ($P_A$) comprises or consists of type I collagen and is dissolved in a polymer solvent ($S_A$) consisting of an acidic aqueous solution, e.g. having a pH of about 3. The effective concentration of collagen in the polymer solution ($S_A$) is preferably in the range from 0.1 to 1.5 (w/v) %.

The second polymer ($P_B$) is preferably a synthetic polymer, more preferably selected from the group consisting of poly(glycolic acid), poly(lactic acid), poly(glycolic acid-lactic acid) and mixtures thereof. Polymer components of lactic acid (PLA), for example, poly-L-lactic acid (PLLA), poly-D,L-lactic acid (racemic mixture of L- and D-lactides; PDLLA), poly-glycolic acid (PGA) or mixtures thereof (PLGA; now also termed poly (lactide-co-glycolide) or PLG) are attractive candidates for fabricating biodegradable matrices due to their flexible and well defined physical properties and relative biocompatibility.

Additionally, their degradation products are low molecular weight compounds, such as lactic acid and glycolic acid, which enter into normal metabolic pathways. Furthermore, copolymers of poly(lactic-co-glycolic acid) offer the advantage of a large spectrum of degradation rates from a few days to years by simply varying the copolymer ratio of lactic acid to glycolic acid.

In a particularly preferred embodiment, the second polymer ($P_B$) is a copolymer of PLLA and PGLA. The properties of these polymers can be tuned by changing the polymer composition within the basic PLLA/PLGA theme. In one embodiment, the second polymer ($P_B$) is preferably poly (glycolic acid-lactic acid) having a lactic acid content of about 85 mol % and a glycolic acid content of about 15 mol %. Such a 85/15 mixture of poly(lactid acid) (PLLA) and poly(lactide-co-glycolide) (PLGA) can be purchased, for instance, from Evonik Industries AG (Essen, Germany) or from Durect company (Cupertino, Calif., USA). Further preferred polymer mixtures for use as second polymer ($P_B$) are poly(D,L-lactide-co-glycolide) 50:50, e.g. RESOMER® RG 502; poly(D,L-lactide-co-glycolide) 65:35, e.g. RESOMER® RG 653; poly(D,L-lactide-co-glycolide) 75:25, e.g. RESOMER® RG 752; poly(D,L-lactide-co-glycolide) 85:15, e.g. RESOMER® RG 858 or LACTEL® Absorbable Polymers.

As mentioned in the introductory portion of this application, preparation methods for preparing porous scaffolds from the above-mentioned synthetic polymers are well known in the art. One possibility is the use of a salt-leaching technique, as described, for instance in EP 2256155.

Further to the method defined in claim 1 of the present application, the present invention also relates to a three-dimensional polymer scaffold (3D-PS) obtainable by the method. In particular, the invention relates to a three-dimensional polymer scaffold (3D-PS) prepared in accordance with the method of the present invention that is essentially free from glutaraldehyde.

In this regard, the term "essentially free" means that the concentration of glutaraldehyde on the three-dimensional polymer scaffold is 0.21 mg/m$^3$ at most. This means that the concentration of glutaraldehyde is below the threshold limit value (TLV) of 0.05 ppm. Preferably, the concentration of glutaraldehyde is below 0.0001 ppm, most preferably less than 1×10$^{-6}$ ppm.

It is further preferred that the three-dimensional polymer scaffold (3D-PS) prepared in accordance with the method of the present invention is hydrophilic, meaning that it has a hydrophilic surface with a contact angle of water that is below 35°, more preferably below 30°. Generally, the contact angle of a three-dimensional polymer scaffold of the present invention will lie within the range of 15° to 25°.

As regards the structure of the three-dimensional polymer scaffold (3D-PS), i.e. the direct product of the method of the present invention, it is preferred it that has an overall porosity of at least 80%, preferably of at least 90%. This allows for a diffusion of gases, e.g. oxygen, liquids and (macro-)molecules, such as cells nutrients and waste, through the polymer scaffold, which is essential for allowing and promoting cell proliferation on the polymer scaffold.

The three-dimensional polymer scaffold obtainable by the method of the invention further preferably comprises pores with a pore size diameter range of 10 to 900 µm, preferably of 50 to 600 µm, most preferably of 200 to 400 µm.

The size of a pore can be specified by means of its average pore diameter—that is the mean of the longest and shortest diameters of the pores which can be discerned in a two-dimensional section. Pore size and pore distribution can be determined by means of scanning electron microscope (SEM), for instance, in a manner well known to the skilled person.

According to a further aspect, the present invention also relates to the use of the three-dimensional polymer scaffold prepared in accordance with the method described above for infiltration with cells in a therapeutic method for treatment of the human or animal body, preferably as an implant in tissue engineering.

In order to further facilitate the attachment of cells to the surface of the three-dimensional polymer scaffold, the polymer scaffold may further be provided with a hydrophilic plasma coating by plasma treatment before cells are loaded onto the scaffold. Most preferably, the polymer scaffold is provided with a thin coating by plasma deposition of a polymerized substance, preferably selected from the group of (methyl)-acrylate (MA), (methyl)-acrylate anhydride (MAA) and poly(2-hydroxyethylmethacrylate) (PHEMA).

The three-dimensional polymer scaffold may also be provided with additional stimulating or growth factors, such as vessel growth factors (VGF), which help to stimulate and attract cells that lead to the formation and ingrowth of small vessels (capillaries) into the polymer scaffold.

In order to increase the number of cells that can be loaded onto the polymer scaffold, the three-dimensional polymer scaffold obtainable by the method of the present invention may also be provided as a thin sheet, e.g. of 1 mm height or thickness, that is then loaded with cells on at least one side, preferably on both sides (top surface and bottom surface), and may subsequently be folded to form a tubular structure and/or multi-layer-structure. For instance, in one embodiment, several tubes formed from three-dimensional polymer scaffolds loaded with cells may be assembled to form a system of pipes mimicking blood vessels and the like.

In a still further aspect, the present invention further pertains to the use of low-pressure plasma treatment for the removal of glutaraldehyde from a polymeric precursor scaffold (p-PS) comprising at least one biodegradable natural polymer ($P_A$) selected from the group consisting collagen, gelatin, laminin, fibrinogen, albumin, chitin, chitosan, agarose, hyaluronic acidalginate and mixtures thereof, by exposing the polymeric precursor scaffold (p-PS) to an ionized oxygen-containing gas plasma at a temperature below 40° C.

Preferred embodiments of method and of three-dimensional polymer scaffold according to the invention will now be exemplified and illustrated by way of the accompanying drawing and the following examples.

EXPERIMENTAL

Preparation of the Basic Polymer Scaffold by Salt Leaching Process 1 g polymer material of the first biocompatible polymer (PLGA or PLLA) was filled in a glass tube and dissolved in 5 ml of chloroform to prepare 20 (w/v) % solutions. The tube was incubated in an orbital shaker incubator at 37° C., 150 rpm for 3 to 5 hours.

Sodium chloride (NaCl) particulates were ground using mortar and pestle before being sieved to obtain NaCl particulates ranging from 355 to 425 µm. 9 g NaCl particulates were put in a centrifuge tube and dried in a desiccator. The NaCl particulates were then put into an aluminum pan and the dissolved PLGA/PLLA-chloroform solution was poured onto the NaCl particulates. The chloroform was evaporated in a fume hood. The PLLA/PLGA-NaCl composites were detached from the aluminum pan and dried in a vacuum chamber under −0.1 MPa for 3-4 days.

The resulting scaffolds were put in a beaker, immersed in ddH$_2$O (twice deionized water) and kept in a linear shaking bath at 25° C. (room temperature), at 60 rpm for 48 hours to leach/wash out the NaCl particulates. The water in the beaker was exchanged every 1-2 hours. The scaffolds were removed from the beaker and dried in the fume hood overnight to afford the basic polymer scaffolds (bPS).

Surface Coating of Basic Polymer Scaffold with Collagen

The basic polymer scaffolds were cut to round scaffolds having a diameter of 2 cm. These round-shaped basic polymer scaffolds were immersed in 20 ml collagen solution (0.5% Collagen Type I Solution; Wako) in a centrifuge tube, put under reduced pressure using a vacuum freeze dryer to remove air from the primary pores, such that the primary pores were filled with collagen solution. The scaffolds were then removed from the collagen solution and placed on cell strainer membranes in 50 ml centrifuge tubes. The scaffolds were centrifuged for 5 minutes at 2000 G, 4° C., to remove any excess collagen solution, turned over and centrifuged again for 5 minutes. The scaffolds were placed in a petri dish 55 mm and frozen in a deep freezer at −80° C. for several hours before freeze-drying under a vacuum of <5 Pa for at least 24 h. The collagen-coated polymer scaffolds, i.e. the precursor polymer scaffolds (p-PS), were sealed in a plastic bag and stored in a refrigerator until further use.

Covalent Cross-Linking of Collagen within Primary Pores of Basic PLLA/PGLA Scaffolds 25-30 ml of 25% glutaraldehyde aqueous solution were put into a petri dish (100 mm) inside a closable plastic box. The closed plastic box was placed into the fume hood and kept inside for 0.5 h to create a glutaraldehyde atmosphere inside the plastic box as glutaraldehyde evaporates from the aqueous solution. The collagen-coated precursor PLLA/PGLA scaffolds (p-PS) were then placed into the plastic box, around the petri dish with the glutaraldehyde solution and incubated with the glutaraldehyde vapour inside the box at 37° C. for 4 h. This resulted in a covalent cross-linking of collagen to the basic PLLA/PGLA scaffold within the primary pores, affording cross-linked polymer scaffolds (x-PS).

Glycine Blocking Step to Block Unreacted Glutaraldehyde Groups

A glycine solution was prepared as follows: 0.75 g of glycine was poured into a glass bottle filled with 100 ml of ddH2O. The bottle was placed inside linear shaking bath (60 rpm) for 30 minutes to dissolve the glycine.

The cross-linked collagen-PLLA/PGLA scaffolds (x-PS) were put into 20 ml of 0.1 M glycine solution in a centrifuge tube and degassed in the vacuum freeze dryer to immerse the scaffolds within the of glycine solution. The tubes were placed in the linear shaking bath (60 rpm) for at least 4 h. Then the scaffolds were washed with ultrapure water (ddH2O) 25 ml in a centrifuge tube and put in the linear shaking bath (60 rpm) for another 4 h. (The water in the centrifuge tube was changed every hour).

The scaffolds were removed from the washing solution and frozen at −80° C. for at least 4 h before freeze-drying under vacuum (<5 Pa) for at least 24 h. The resulting cross-linked polymer scaffolds were stored in a desiccator or in a refrigerator (in a plastic bag).

Alternatively, instead of an aqueous glycine solution, gaseous glycine was used as blocking agent: To this end, the cross-linked polymer scaffolds were placed into a tubular container having an inlet on one end and an outlet at the other. Liquid glycine was poured into a glass bottle and the lid was closed using a septum. Two pipes were installed that led through the septum: an inlet pipe connected to an oxygen and argon source on one end and having the other end dipped into the glycine within the bottle, and an outlet pipe leading out of the bottle and into the tubular container containing the polymer scaffold. The bottle containing the glycine was then heated until the glycine started to evaporate. Argon and oxygen was fed through the inlet pipe into the glycine within the bottle, such that a mixture of oxygen, argon and gaseous glycine was forced out of the container through the outlet pipe. From the outlet pipe, the oxygen/argon/glycine gas was fed via the inlet into the tubular container, through the polymer scaffold and discharged through the outlet. A vacuum pump connected to the outlet of the tubular container helped sucking the oxygen/argon/glycine gas through the polymer scaffold and out of the tubular container.

Plasma Treatment

For clinical application, the cross-linked polymer scaffolds obtained after the glycine blocking step were further processed by plasma treatment to afford the desired three-dimensional polymer scaffolds (3D-PS). The scaffolds were first degassed under vacuum to remove or evacuate any remaining glutaraldehyde residue.

Plasma treatment was conducted with the aid of a FEMTO Low pressure plasma system from Diener Electronics GmbH & CO KG (DE).

In general, plasma treatment takes place in an apparatus that comprises an evacuable vacuum chamber with a generator device and electrodes for generating a low-pressure plasma in the interior of the vacuum chamber.

The generator device is a unit providing the voltage (mostly alternating) for the excitation of the plasma. Due to the frequency of the alternating voltage, LF generators (40 kHz), HF generators (13.56/27.12 MHz) and Microwave generators (2.45 GHz) are distinguished. The electrodes provide an electric conductor, through which an electric current generated by the generator device is conducted for ionization of the process gas, generating a plasma.

The plasma treatment process generally involves the following main steps:
1. Step: Evacuation of the vacuum chamber (recipient);
2. Step: Admission of a process gas and ignition of the plasma;
3. Step: Ventilation of the recipient and removal of the sample.

In respect of the present invention, the plasma treatment will be explained with reference to FIG. 1:

FIG. 1 shows a schematic depiction of a plasma treatment process;

In a first step, scaffold samples 1 were placed in a recipient 3 and the latter was evacuated with the aid of a vacuum pump 5, thereby creating a low or negative pressure inside the recipient 3.

In step 2, a process gas (i.e. oxygen) 8 was fed from a supply tank 9 into the recipient 3 at a pressure of approx. 0.1 mbar. When a working pressure within the range of 0.1 to 1.0 mbar was achieved, a high-frequency generator (13.56 MHz) 9 was switched on and the process gas 8 in the recipient 3 became excited by energy input from the generator 9 through an electrode 11. This caused high energy ions and electrons to developed along with other reactive particles; forming an oxygen plasma 13 within the recipient 3. The oxygen plasma 13 reacted chemically with the surface of the scaffold sample 1 during exposure of the latter to the oxygen plasma 13. Fresh process gas 8 was supplied continuously to the plasma process and contaminated gas 14 was extracted.

After an exposure time ranging from 2 to 30 min, the surface of the scaffold sample 1 showed to be cleaned and activated.

Subsequently, in step 3, the recipient 3 was vented by introducing a hydrogen peroxide 15 as process gas into the chamber 3 and the scaffold sample 1 was sterilized within the hydrogen peroxide atmosphere for 16 hours.

Throughout the whole plasma treatment and sterilization process, the temperature within the recipient was held below 35° C.

The invention claimed is:

1. A method for preparing a three-dimensional polymer scaffold for use in tissue-engineering, the method comprising:
   a) providing a polymeric precursor scaffold (p-PS) comprising at least one biodegradable natural polymer ($P_A$);
   b) treating the polymeric precursor scaffold (p-PS) with a cross-linking agent comprising glutaraldehyde to induce cross-linking of the natural polymer ($P_A$), thereby forming a cross-linked polymer scaffold (x-PS);
   c) treating the cross-linked polymer scaffold (x-PS) with aqueous or gaseous blocking agent selected from the group consisting of glycine and glutamic acid to block non-reacted glutaraldehyde groups;
   d) then treating the cross-linked polymer scaffold (x-PS) under reduced pressure by multiple applications of a vacuum, where each application is for less than 1 ms, or freeze-drying the cross-linked polymer scaffold (x-PS) to remove excess glutaraldehyde;

e) then subjecting the cross-linked polymer scaffold (x-PS) to low-pressure plasma treatment involving exposure of the polymer scaffold to an ionized oxygen-containing gas plasma at a pressure in the range of $10^{-3}$ to $10^{-6}$ bar and a temperature below 40° C., affording the three-dimensional polymer scaffold (3D-PS); and f) then sterilizing the three-dimensional polymer scaffold (3D-PS) after exposing the three-dimensional polymer scaffold (3D-PS) in step e) to hydrogen peroxide at a temperature below 40° C. for a time period of at least 1 hour.

2. The method according to claim 1, wherein in step e), the cross-linked polymer scaffold (x-PS) is subjected to plasma treatment for a period in the range of 0.5 to 60 minutes.

3. The method according to claim 1, wherein in step d), the cross-linked polymer scaffold (x-PS) is treated under reduced pressure by multiple applications of the vacuum, where each application is for less than 0.1 ms.

4. The method according to claim 1, wherein, prior to the sterilization step, the three-dimensional polymer scaffold (3D-PS) of step e) is exposed to a second ionized gas plasma that is different from the first gas plasma and is at least one selected from the group consisting of helium, argon, nitrogen, neon, silane, hydrogen, and oxygen.

5. The method according to claim 1, wherein an ionized hydrogen peroxide gas plasma is used.

6. The method according to claim 1, wherein the natural polymer ($P_A$) is at least one selected from the group consisting of collagen, gelatin, laminin, fibrinogen, albumin, chitin, chitosan, agarose, and hyaluronic acid-alginate composite.

7. The method according to claim 1, wherein the polymeric precursor scaffold (p-PS) provided in step a) further comprises a second biodegradable polymer ($P_B$) different from natural polymer ($P_A$), whereby the polymeric precursor scaffold (p-PS) is prepared by:

i) providing a porous basic polymer scaffold (bPS) made from at least the second biodegradable polymer ($P_B$);

ii) introducing a polymer solution comprising the biodegradable natural polymer ($P_A$) dissolved in a polymer solvent ($S_A$) into pores of the basic porous scaffold (bPS), whereby the concentration of the natural polymer ($P_A$) in the polymer solvent ($S_A$) is in the range from 0.1 to 5.0 w/v %; and iii) removing the polymer solvent ($S_A$) under reduced pressure.

8. The method according to claim 7, wherein the second polymer ($P_B$) is at least one synthetic polymer selected from the group consisting of poly(glycolic acid), poly(lactic acid), and poly(glycolic acid-lactic acid).

* * * * *